United States Patent [19]

Nagodawithana et al.

[11] Patent Number: 4,530,846

[45] Date of Patent: Jul. 23, 1985

[54] METHOD FOR THE PRODUCTION OF SELENIUM YEAST

[75] Inventors: Tilak Nagodawithana, Bayside; Feliks Gutmanis, Milwaukee, both of Wis.

[73] Assignee: Universal Foods Corporation, Milwaukee, Wis.

[21] Appl. No.: 466,398

[22] Filed: Feb. 15, 1983

[51] Int. Cl.$^3$ ............................................. A23L 1/28
[52] U.S. Cl. ................................... 426/62; 435/940; 435/942
[58] Field of Search .................. 435/942, 940; 426/62

[56] References Cited

PUBLICATIONS

Yoshida et al.–Chem. Abst., vol. 89, (1978), p. 41095r.
Uragami–Chem. Abst., vol. 91, (1979), p. 54612y.

*Primary Examiner*—Sam Rosen
*Attorney, Agent, or Firm*—Neuman, Williams, Anderson & Olson

[57] ABSTRACT

A process for preparing selenium yeast having a high intracellular selenium content is provided which comprises the continuous incremental feeding of nutrients and selenium compounds to yeast during the growth cycle.

13 Claims, No Drawings

METHOD FOR THE PRODUCTION OF SELENIUM YEAST

FIELD OF THE INVENTION

This invention relates to a method for the preparation of yeast containing substantial amounts of intracellular organically bound selenium, useful as a supplementary diet source of metabolizable selenium where additional selenium is indicated.

DESCRIPTION OF THE PRIOR ART

While the role of selenium in mammalian diets is not completely understood, certain investigative work has indicated that selenium supplemented diets can play a role in the prevention of certain conditions in mammals. For example, food yeast such as *Saccharomyces cerevisiae* and *candida utilis* which incorporate selenites during growth, when dried and fed to rats, effectively prevent hepatic liver necrosis. See, Reed et al., *Yeast Technology* AVI Publishing Co. (Conn. 1973) p. 41. More recently, experiments have been conducted indicating that organically bound selenium in the diets of mammalians can be a factor in prevention of cancer.

The use of selenium in mammalian diets is limited, however, by virtue of the fact that many inorganic and organic selenium compounds such as salts are highly toxic and cannot be consumed in substantial amounts by mammals in that form, particularly as inorganic compounds. It is known, however, that selenium compounds may be used as an additive component of the nutrient substrate for growing certain food yeasts such as baker's yeast or *Saccharomyces cerevisiae* to produce yeasts that contain intracellular selenium compounds in an organically bound ingestible form whose exact composition is not known. The organically bound intracellular selenium as it is found in yeast that has been grown in a selenium rich nutrient is readily assimilable and efficient as a dietary source of selenium in mammalian diets without exhibiting the normal toxic consequences associated with diets containing supplemental selenium compounds in other chemical forms particularly as inorganic selenium.

Inasmuch as there has been considerable interest in obtaining a form of selenium which can be introduced into the diet as a supplement in substantial quantities without the aforenoted toxic consequences, it would be desirable to produce a food source containing selenium and more particularly a food yeast which contains an intracellular non-toxic assimilable form of selenium to be used as a dietary supplement for mammals including humans.

It has been found that the introduction of selenium salts as a component of the nutrient substrate of yeasts produced by conventional batch processing results in a substantial amount of the selenium being absorbed by the yeast in an organic and biologically combined form that is both assimilable and non-toxic to mammals which subsequently ingest the selenium yeast as a dietary supplement.

The production of selenium yeast by such procedures, however, is limited by a number of factors. For example, high concentrations of selenium salts in the nutrient substrate used to grow the yeast has an inhibitory effect on the growth of yeast and consequently the ultimate yield of yeast (based on molasses) that may be obtained by that procedure. Furthermore the amount of selenium in the yeast recovered by the aforenoted batch yeast growth process in the desired organically bound form is relatively low. Finally, it has been determined that the selenium in recovered yeast produced by the aforenoted batch-feeding technique has an undesirably high potential free selenium toxicity risk as established by the Methylene Blue Reduction Test.

OBJECTS OF THE INVENTION

Accordingly, one of the objects of the present invention is the provision of a method for producing a selenium yeast having an enhanced intracellular selenium content.

Another object is the provision of a method for producing a food yeast having high levels of organically bound intracellular selenium in an assimilable non-toxic form.

A further object is the provision of a method and process for producing an edible food yeast product having a high intracellular selenium content which is useful as a dietary supplement.

A final object is the provision of a food yeast having a uniformly distributed intracellular selenium content of high concentration, but which is essentially free of the toxic risk of free selenium as established by the Methylene Blue Reduction Test.

SUMMARY OF THE INVENTION

The foregoing objects are achieved by a process and method for preparing an edible selenium yeast product which has a high intracellular, organically bound, assimilable selenium content, which process comprises continuously and incrementally feeding a substantial quantity of a soluble selenium salt to a food yeast such as *Saccharomyces cerevisiae* maintained in a growth medium under aerobic yeast growth conditions in conjunction with the incremental addition of a carbon nutrient source such as molasses wort, to said medium, to support the growth of the yeast. The growth medium is further characterized by low levels of inorganic sulfur nutrients. "Low levels" of inorganic sulfur means less than about 0.5% and preferably about 0.1% to 0.2% sulfur on a yeast solids basis. Broadly however, the inorganic sulfur content of the nutrient media should be maintained at sufficiently low levels so as not to substantially adversely affect the yield of yeast produced by the process.

After the growth cycle is completed, the yeast is harvested from the fermenter such as by centrifugation and washed essentially free of extracellular, water-soluble residual selenium compounds to produce an edible selenium yeast which is characterized by an intracellular organically bound selenium content of at least 1000 ppm and characterized by being essentially free of extracellular inorganic selenium as determined by the Methylene Blue Reduction Test.

Yeast products with intracellular selenium contents of 1000 ppm or more are achieved by the continuous incremental feeding of soluble selenium compounds to the nutrient growth media for the yeast at levels which are as high as 128 ppm on a fermenter volume basis or about 0.4% Se in the molasses which is incrementally fed to the fermenter. The selenium salt addition is conveniently carried out in the last or final fermenter stage of commercial yeast propagation, sometimes called the "trade" fermenter in the context of conventional commercial multi-batch yeast fermentation processes but may be carried in any isolated yeast growth fermentation procedure.

It should be understood that at any given time in the fermentation process, the concentration of selenium salt should not be as high as to inhibit the growth of the yeast. In this context, it has been found that periodic additions of selenium salts at selected intervals, i.e., at the 8½, 9th, 9½, and 10th, hours of fermentation at the high levels calculated to achieve an intracellular selenium content in the harvested yeast of about 1000 ppm or more, resulted in a reduction of the yeast yield (based on molasses) to levels of about 40% and additionally resulted in a lower level of intracellular selenium in the final yeast produced by that procedure. It has been found that incremental addition of the selenium salt throughout the yeast fermentation and growth process obviates these undesirable adverse results. The continuous incremental addition of the selenium salts or compounds can readily be carried out by mixing the selenium compounds with the molasses feed (wort) which is also continuously added to the yeast fermenter. This procedure usually requires temperatures of less than about 120° F. (45° C.) to avoid possible degrading of the selenium compound, e.g., sodium selenite. If the wort temperature used in the method are above about 120° F. (45° C.), then the selenium salts (if unstable at higher temperatures) are preferably added separately (as in a solution) as a continuous incremental feed to the fermenter simultaneously and concurrently with the addition of the carbon source nutrient throughout the entire fermentation period, e.g., over a time period of from 14 to 16 hours.

A typical commercial operation for producing yeast is described in Reed & Peppler, *Yeast Technology*, pp. 79-80 (1973). That process starts in the laboratory, where Pasteur flasks containing a rich medium (malt extract or malt extract molasses blend) are inoculated from slants of the pure yeast culture. The contents of the Pasteur flasks, after typically two (2) to three (3) days incubation is then inoculated into small pure culture fermenters usually a series of three pure culture fermenters with capacities of, e.g., 20 gal., 100 gal., and 1000 gal. The yeast is grown in these fermenters in a sterile medium rich in growth factors. There is no incremental feeding of nutrients and/or molasses in this growth stage and little aeration. The air used is customarily sterilized. The last pure culture stage has been designated the (F1) stage.

The pure culture fermenter stages are followed by one or more incrementally fed stages (F2, F3, etc.). A portion of the fermenter contents of the (FI) stage is pumped into a larger tank for the first incrementally fed stage (F2). From this point on in the yeast propagation system, aeration is vigorous and molasses and other nutrients are fed incrementally. After completion of each of these incrementally fed stages of fermentation, the yeast is separated from the bulk of the fermenter liquid (beer) by centrifuging, producing a stock of yeast for the next stage. The fermenter contents of a completed incrementally fed stage is usually divided into several parts for pitching of the next stage of fermentation. After the final incrementallly fed stage of fermentation, also called the "trade" stage, the yeast is removed from the fermenter beer by centrifugation to produce a yeast cream of 13–16% solids and washed. In the present process, the yeast is washed up to as many as seven (7) to ten (10) times or as necessary to reduce or substantially remove the extracellular nutrients and extracellular selenium salts from the yeast by re-suspending the yeast in water (diluted in ratios of about 1:10 when washing is completed the yeast is reduced in the moisture content to a cream (16% yeast solids) followed by pasteurizing and drum drying so as to reduce its moisture content to about 4 to 5% to produce a dried yeast product. The pasteurization should be carried out at 85° C. for 45 minutes in cream stage or similar or equivalent conditions to non-viable yeast product.

Incremental feed, as used above, refers to the practice of adding the molasses and other nutrients to the fermenter liquid-yeast mixture preferably at such a rate that the molasses is consumed by the yeast at the same rate it is added. Since the yeast population increases with the growth cycle, the rate at which the nutrient added is consumed is also increased. In the process of this invention, the selenium salts are added continuously and incrementally as a separate feed or admixed with the molasses wort, by the technique discussed above.

The dried yeast is tested for extracellular inorganic selenium by the Methylene Blue Reduction Test (MBRT) which involves the following test procedure.
1. Place in vial, 0.5 g powder or sample containing approximately 100 μg Se in product.
2. Add 5 mls of "Reducing Solution" containing 20% solution of 1-thioglyercol in 0.2N phosphate buffer pH 5.5.
3. Shake closed vial for 10 seconds.
4. After 3 minutes, at t=0, add 2 drops of Methylene Blue solution containing 2% w/v Methylene Blue in doubly distilled water.
5. Close the vial and shake for 10 seconds.
6. Record time at which decolorization is essentially complete. This is referred to as MBRT time.

The time of test indicates the presence of inorganic selenium. More than fifteen (15) or twenty (20) minutes indicates a sufficiently low extracellular inorganic selenium content. For example, baker's yeast without any selenium will give an MBRT of ninety (90) to one hundred fifty (150) minutes. Yeasts with substantial extracellular selenium, e.g., 10 ppm. will give MBRT times of from 0.5 to 7 minutes.

In the present process the selenium salts used are water-soluble selenium compounds, preferably inorganic compounds of which sodium selenite ($Na_2SeO_3$) is preferred. Other selenium compounds which may be used are $Na_2SeO_4$. The total quantity of selenium added during the yeast growth in the fermenter is about 0.15 to 40% based on final dry yeast solids produced, preferably 0.2 to 0.25% and most preferred at about 0.22% selenium based on final dry yeast.

Additionally, the procedures of the present invention are carried out without the addition of ammonium sulfate and without the use of sulfuric acid for pH adjustment which procedures are conventional in commercial yeast manufacture processes.

DESCRIPTION OF THE PREFERRED EMBODIMENT

The following Examples 1–6 illustrate the results obtained by the use of the method of the present invention, in the propagation of selenium yeast in a ten (10) liter fermenter, as contrasted with other procedures (Examples 7) wherein a selenium salt was fed periodically to the fermenter.

In Examples 1–6, a calculated amount (2800 mg.) of water-soluble selenium compound, particularly sodium selenite ($Na_2SeO_3$) was mixed with 1600 grams of molasses wort used as the carbon source nutrient added continuously over a fermentation period of 16½ hours and was added to the yeast pitch (65 grams) in 7000 ml of water in a ten (10) liter fermenter. The nutrient medium had the following initial composition.

| Water | 7000 ml. |
|---|---|
| $NH_4Cl$ | 44 grams |
| $NH_4H_2PO_4$ | 16.8 grams |
| $MgSO_4.7H_2O$ | 3.4 grams |
| KCl | 3.7 grams |
| thiamine | 90 mg. |
| Yeast | 65 grams |
| (*Saccharomyces cerevisiae*) | |

Sixty milligrams of $ZnSO_4.H_2O$ was added to the 1600 grams of molasses used. Ammonium hydroxide was added on demand to maintain pH at 5.2 (approximately 100 mls. of 29.8% ammonium hydroxide) throughout fermentation. Temperatures were maintained at about 29°–30° C. Aeration was continuous throughout the process to maintain aerobic yeast growth condition.

When the fermentation was complete, the yeast was separated, washed seven (7) times with water (1:10 dilution), reduced in moisture content to a yeast cream (16–18% yeast solids) and pasteurized at 85° C. for forty-five (45) minutes followed by drum drying to a final moisture content of about 4.5% (based on dry yeast solids). The results are shown below in Table I below.

TABLE I

| | $Na_2SeO_3$ Fed with Wort (0–16.5 Hours) in 10 liter batches | | | | | |
|---|---|---|---|---|---|---|
| Example | 1 | 2 | 3 | 4 | 5 | 6 |
| $Na_2SeO_3$ enrichment, mg/fermenter | 2800 | 2800 | 2800 | 2800 | 2800 | 2800 |
| Se enrichment, mg/fermenter | 1279.6 | 1279.6 | 1279.6 | 1279.6 | 1279.6 | 1279.6 |
| Se conc. in fermenter beer, μg/ml (ppm) | 127.96 | 127.96 | 127.96 | 127.96 | 127.96 | 127.96 |
| Yeast production, g yeast solids/ferm. | 420.2 | 420.0 | 414.4 | 411.5 | 410.8 | 422.0 |
| Yield % (based on 85° Brix molasses) | 72.4 | 72.5 | 71.3 | 70.7 | 70.5 | 72.7 |

EXAMPLE 7

In another batch yeast fermentation, the sodium selenite was added directly to the yeast fermenter in four increments at 8.5, 9.0, 9.5 and 10.0 hours of aerobic yeast growth was also made. Otherwise the fermentation procedures were the same as shown for Examples 1–6 above. Table II shows the results of this fermentation.

TABLE II

| | $Na_2SeO_3$ Added In Four Increments (See Above) |
|---|---|
| $Na_2SeO_3$ enrichment, (mg/fermenter) | 2625 |
| Se enrichment, (mg/fermenter) | 1200 |
| Se conc. in fermenter beer, μg/ml (ppm) | 120 |
| Yeast production, in grams of yeast solids/fermenter | 260 |
| Yield percentage (based on 85° Brix molasses) | 44.2 |

[The low yield of yeast (44%) is contrasted with the higher yields (70–73%) in Examples 1–6].

Table III is a comparison of the composition of the yeast produced from a composite of the yeasts shown in Table I (Examples 1–6) with the yeast product of Example 7 and Table II from the point of view of selenium enrichment of the yeast and the Methylene Blue Reduction Test.

| COMPARISON OF YEAST DATA FROM TABLES I AND II | | |
|---|---|---|
| | EXAMPLES 1–6 | EXAMPLE 7 |
| Se content in dried yeast, μg/g (ppm) | 2000 | 1440 |
| Methylene Blue Reduction Test (MBRT), min.* | 90 | 0 |
| Total Se recovered in yeast solids, mg | 4997.8 | 386.1 |
| Se enrichment used, mg | 7677.6 | 1200 |
| Se recovery, % | 65.1 | 32.2 |
| N in yeast, % | 9.51 | 4.86 |
| $P_2O_5$ in yeast, % | 3.05 | 3.31 |

*A time of fifteen (15) minutes or greater in the MBRT test is the acceptable level for indicating that the selenium is organically bound.

From the foregoing, it is evident that high contents of organically bound intracellular selenium in yeast can be attained by feeding selenium continuously and incrementally and simultaneously with a carbon source nutrient to the yeast throughout during the yeast growth.

The principles of the process of the present invention may be applied to other food grade or edible yeasts other than the illustrated baker's yeast or *Saccharomyces cerevisiae*, such as for example, brewer's yeast or *Saccharomyces uvarum* or the like. While intracellular selenium contents of yeasts are preferably in the range of 1000 ppm, or more, even as high as 2500 ppm, the process has, as its practical limitations, the capacity of the yeast to assimilate the selenium during the yeast growth cycle without adverse effects on yield due to the selenium additive to the nutrients.

It should also be understood that the principles of maintaining low levels of inorganic sulfur in the nutrient media is broadly applicable to the process of producing selenium yeasts. For this reason, adjustment of pH should avoid the use of sulfuric acid as a pH regulator, in favor of non-sulfur containing pH adjustment reagents such as hydrochloric acid.

What is claimed is:

1. A process for producing an edible selenium yeast product suitable for mammalian consumption having an organically bound selenium content of at least about 1000 ppm on a dry yeast weight basis which comprises:
    (a) propagating a food grade yeast by maintaining the yeast under aerobic yeast growth conditions in a fermenter;
    (b) continuously and incrementally providing said yeast with an assimilable carbon source nutrient added to said yeast in the fermenter wherein the inorganic sulfur content in the nutrient medium is maintained at levels sufficiently low so as to not substantially affect the yield of yeast;

(c) simultaneously and continuously adding in conjunction with the addition of said nutrient, a water-soluble selenium salt that is relatively non-toxic to said yeast cells at concentrations sufficient to provide a final concentration of assimilable organically bound intracellular selenium in said yeast of at least 1000 ppm on a dry yeast solids basis;

(d) recovering the selenium yeast so formed from the fermenter when the yeast growth has reached a predetermined level;

(e) washing the recovered selenium yeast to remove extracellular nutrients and extracellular selenium salts therefrom; and (f) pasteurizing and drying the washed yeast cells to recover a dried selenium yeast product containing a substantial amount of assimilable organically bound, intracellular selenium and essentially free of extracellular inorganic selenium.

2. A process according to claim 1 wherein said selenium yeast product is substantially free of inorganically bound selenium as shown by a Methylene Blue Reduction Test result of fifteen (15) minutes or greater.

3. A process according to claim 1 wherein the selenium salt is added to the fermenter in admixture with an assimilable carbon source yeast nutrient where said nutrient has a temperature below 45° C.

4. A process according to claim 1 wherein said yeast growth carbon source nutrient is molasses.

5. A process according to claim 1 wherein said selenium salt is sodium selenite.

6. A process according to claim 1 wherein said sodium selenite is sodium selenate.

7. A process accordiing to claim 1 wherein the yeast growth carbon source nutrient is a carbohydrate.

8. A process according to claim 1 wherein the pH of the aqueous yeast suspension is adjusted with ammonium hydroxide during the growth cycle.

9. A process according to claim 1 wherein the yeast growth is maintained for a period from about ten (10) to about eighteen (18) hours.

10. A process according to claim 1 wherein the yeast is *Saccharomyces cerevisiae*.

11. A process according to claim 1 wherein the yeast is brewer's yeast (*S. Uvarum*).

12. A process according to claim 1 wherein the yeast fermentation is carried out in a nutrient medium wherein the inorganic sulfur content is maintained at levels of less than about 0.5%.

13. A method of preparing an edible selenium yeast product which has a high intracellular organically bound, assimilable selenium content which comprises:

(a) adjusting the pH of an aqueous suspension of live, edible, food grade yeast cells from about 4.5 to about 6 maintained in a fermenter;

(b) adding a water-soluble selenium salt simultaneously and incrementally in conjunction with the continuous and incremental addition of a yeast growth carbon source nutrient medium under fermentation conditions which are essentially free of sulfuric acid and ammonium sulfate and wherein the total inorganic sulfur content in the nutrient medium is maintained at levels of less than about 0.5%, to thereby promote growth of said yeast cells and to enhance the intracellular selenium content of said yeast to at least 1000 ppm on a dry yeast basis;

(c) recovering and concentrating the selenium yeast cells from the aqueous growth medium;

(d) washing the recovered yeast cells to remove extracellular selenium salts; and (e) pasteurizing and drying the washed yeast cells to produce a yeast product which is essentially free of extracellular selenium as determined by a Methylene Blue Reduction Test time of more than fifteen (15) minutes.

* * * * *